US008993112B2

(12) United States Patent
Elder et al.

(10) Patent No.: US 8,993,112 B2
(45) Date of Patent: *Mar. 31, 2015

(54) POLYMERIC PARTICLES (75) Inventors: Stewart Todd Elder, Butler, NJ (US); Christina Ligia Andrianov, Hawthorne, NJ (US); Kishor Kumar Mistry, Bradford (GB); Janine Andrea Preston, Leeds (GB); Mark Christopher Baxter, Bradford (GB)

(73) Assignee: BASF SE, Ludwigshafen (DE)

( * ) Notice: Subject to any disclaimer, the term of this patent is extended or adjusted under 35 U.S.C. 154(b) by 1064 days.

This patent is subject to a terminal disclaimer.

(21) Appl. No.: 11/629,330

(22) PCT Filed: Jun. 2, 2005

(86) PCT No.: PCT/EP2005/005917
§ 371 (c)(1),
(2), (4) Date: Jun. 25, 2007

(87) PCT Pub. No.: WO2005/123796
PCT Pub. Date: Dec. 29, 2005

(65) Prior Publication Data
US 2007/0255008 A1 Nov. 1, 2007

(30) Foreign Application Priority Data

Jun. 15, 2004 (GB) .................................. 0413338.5
Jul. 30, 2004 (GB) .................................. 0417073.4

(51) Int. Cl.
B32B 5/16 (2006.01)
C08L 25/02 (2006.01)
C08L 25/14 (2006.01)
A61K 8/29 (2006.01)
A61K 8/81 (2006.01)
A61Q 19/00 (2006.01)
C08F 291/00 (2006.01)
C08J 3/12 (2006.01)
C08L 23/08 (2006.01)
C08L 33/12 (2006.01)
C08L 33/02 (2006.01)

(52) U.S. Cl.
CPC . *C08L 25/14* (2013.01); *A61K 8/29* (2013.01); *A61K 8/8152* (2013.01); *A61K 2800/654* (2013.01); *A61Q 19/00* (2013.01); *C08F 291/00* (2013.01); *C08J 3/12* (2013.01); *C08J 2325/14* (2013.01); *C08L 23/0869* (2013.01); *C08L 23/0876* (2013.01); *C08L 33/02* (2013.01); *C08L 33/12* (2013.01)
USPC ............... 428/402; 428/402.22; 428/402.24; 428/407; 525/192; 525/221; 525/222; 525/241

(58) Field of Classification Search
USPC .......... 428/402.21, 402.22, 402.24, 402, 407; 525/192, 221, 222, 241
See application file for complete search history.

(56) References Cited

U.S. PATENT DOCUMENTS

| 3,875,260 | A | * | 4/1975 | Patel et al. ..................... 525/193 |
| 4,076,768 | A | * | 2/1978 | Saunders et al. ................ 525/98 |
| 4,337,185 | A |   | 6/1982 | Wessling et al. ................ 524/458 |
| 4,430,468 | A |   | 2/1984 | Schumacher ................ 524/109 |
| 4,447,475 | A | * | 5/1984 | Lubbock et al. ......... 427/213.31 |
| 4,592,990 | A |   | 6/1986 | Takagi et al. ................. 430/137 |
| 5,133,992 | A |   | 7/1992 | Nair et al. ................. 427/213.34 |
| 5,237,004 | A | * | 8/1993 | Wu et al. ......................... 525/85 |
| 5,306,743 | A |   | 4/1994 | Klesse et al. .................. 523/201 |
| 5,491,195 | A | * | 2/1996 | Schrader et al. ................ 525/71 |
| 5,624,973 | A |   | 4/1997 | Lu et al. .......................... 522/40 |
| 5,866,312 | A | * | 2/1999 | Wang et al. ................... 430/512 |
| 6,087,435 | A | * | 7/2000 | Nakano et al. ................ 524/505 |
| 6,245,483 | B1 | * | 6/2001 | Oshimo et al. ............. 430/281.1 |

(Continued)

FOREIGN PATENT DOCUMENTS

| EP | 0 334 126 | 9/1989 |
| EP | 0 823 458 | 2/1998 |
| GB | 997921 | 7/1965 |
| GB | 2 095 264 | 9/1982 |
| JP | 2-245056 | 9/1990 |
| JP | 2004-18660 | 1/2004 |

(Continued)

OTHER PUBLICATIONS

WPI/Derwent English Language Abstract AN-1990-339164[45] for JP2245056A (Sep. 28, 1990).
WPI/Derwent English Language Abstract AN-2004-261017[25] for JP2004018660A (Jan. 22, 2004).

*Primary Examiner* — Irina Krylova
(74) *Attorney, Agent, or Firm* — Shiela A. Loggins (57) ABSTRACT Polymeric particles comprising a polymeric matrix that has been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., wherein secondary particles are distributed throughout the matrix, in which the secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the polymeric matrix. Also claimed is a process for preparing particles. The particles have improved shatter resistance. Preferably the polymeric particles comprise an active ingredient, especially a colorant. Such particles combine improved shatter resistance with the ability to retain the active ingredient. The particles of the invention can be used in a variety of industrial applications, for instance in the manufacture of inks, paper and cosmetics.

26 Claims, 2 Drawing Sheets

(56) References Cited

U.S. PATENT DOCUMENTS

| | | | |
|---|---|---|---|
| 6,329,057 B1* | 12/2001 | Dungworth et al. | 428/403 |
| 6,387,991 B1 | 5/2002 | Hayes | 24/52 |
| 6,528,473 B1* | 3/2003 | Lannibois-Drean et al. | 510/442 |
| 6,861,484 B2* | 3/2005 | Ganapathiappan | 526/78 |
| 7,217,457 B2* | 5/2007 | Elaissari et al. | 428/407 |
| 2001/0005569 A1* | 6/2001 | Nanpei et al. | 430/287.1 |
| 2002/0058732 A1* | 5/2002 | Mistry et al. | 523/201 |
| 2003/0018102 A1* | 1/2003 | Weston et al. | 523/201 |
| 2004/0136933 A1 | 7/2004 | Mistry et al. | 424/63 |
| 2004/0152618 A1* | 8/2004 | Mistry et al. | 510/475 |
| 2005/0113497 A9* | 5/2005 | Ganapathiappan | 524/160 |

FOREIGN PATENT DOCUMENTS

| | | |
|---|---|---|
| WO | 94/14897 | 7/1994 |
| WO | 01/27209 | 4/2001 |
| WO | 02/090445 | 11/2002 |
| WO | WO 02/090445 | * 11/2002 |

* cited by examiner

Figure 1

Figure 2:
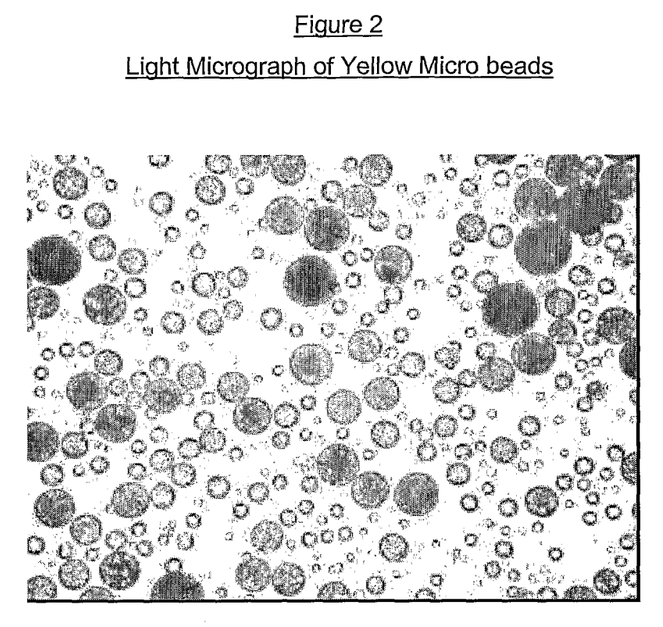

Figure 2
Light Micrograph of Yellow Micro beads

POLYMERIC PARTICLES

JOINT RESEARCH AGREEMENT

Ciba Specialty Chemicals Corp and Procter and Gamble Co. were subject to a Joint Research Agreement at the time this invention was made and the invention was made as a result of work done under that Agreement.

This application is a 0371 National Stage entry of PCT patent application serial number PCT/EP2005/005917 filed on Jun. 2, 2005, which claims priority of GB0413338.5 filed on Jun. 15, 2004 and GB417073.4 filed Jul. 30, 2004 herein incorporated entirely by reference.

The present invention concerns polymeric particles and a process for making them. Polymeric particles of particular interest contain active ingredients especially entrapped colourants.

Entrapment of active ingredients can be achieved by a number of processes. Some of these techniques involve forming a polymeric shell around a central core or active ingredient. Other methods involve preparing a matrix of polymeric material throughout which an active ingredient is distributed.

Various methods for making capsules have been proposed in the literature. For instance it is known to encapsulate hydrophobic liquids by dispersing the hydrophobic liquid into an aqueous medium containing a melamine formaldehyde pre-condensate and then reducing the pH resulting in an impervious aminoplast resin shell wall surrounding the hydrophobic liquid. Variations of this type of process are described in GB-A-2073132, AU-A-27028/88 and GB-A-1507739, in which the capsules are preferably used to provide encapsulated inks for use in pressure sensitive carbonless copy paper.

However, although capsules based on melamine formaldehyde resins are both impervious and durable, they tend to suffer the disadvantage that they are less impermeable at elevated temperatures. In addition there is also a risk that formaldehyde is evolved.

Typical techniques for forming a polymer shell are described in, for instance, GB 1,275,712, 1,475,229 and 1,507,739, DE 3,545,803 and U.S. Pat. No. 3,591,090.

In U.S. Pat. No. 3,838,007 droplets of enzyme dispersed in an aqueous solution of, for instance, gelatin are dispersed into water and then cross-linked, to give cross linked particles of the gelatin containing the enzyme.

In EP-A-356,240 processes for encapsulating enzyme or other biologically produced material; in a matrix of polymeric material by mixing the polymeric material with aqueous liquor containing the biologically produced material, dispersing this mixture in a water immiscible liquid and azeotroping the dispersion. The product can either be relatively coarse beads that can be recovered or a stable dispersion of small particles in the water immiscible liquid.

In EP-A-356,239 there is a description of various compositions and processes primarily intended for the encapsulation of enzymes for liquid or other detergents. One type of product described therein comprises particles having a core comprising matrix polymer containing the enzyme, oil around the core and a polymer shell around the oil.

Particles of a matrix polymer containing an active ingredient can be formed as a dispersion in oil and this dispersion can then be dispersed in aqueous solution of an encapsulating polymer or blend of polymers and polymer deposition can then be caused to occur around the oil particles that contain the particles of matrix polymer that contain the active ingredient.

U.S. Pat. No. 5,744,152 describes a process for forming polymer particles introduced as a solution of a water soluble salt with a volatile amine of a polymer that is relatively insoluble and non-swelling in acid throughout which the active ingredient is dispersed or dissolved, and which the solution is heated to form the dry matrix and to volatilise the amine and thereby form a polymer that is insoluble in acid. The release of an active ingredient can be controlled by careful adjustment of the pH. This method is specifically designed for the entrapment of relatively large sized ingredients, in particular enzymes, fungi, spores, bacteria, cells or antibiotics, which are released by pH adjustment as a suitable release mechanism.

WO 97/24178 describes a particulate composition comprises particles having a polymeric matrix including a detergency active ingredient, wherein the polymeric matrix is formed of a free base form of a cationic polymer which is a co-polymer of an ethylenically unsaturated hydrophobic monomer with an ethylenically unsaturated substituted amine monomer. The matrix particles can be made by polymerising the free base monomer and the hydrophobic monomer while dissolved in an organic solvent so as to form a solution of the free base polymer inorganic solvent. This is followed by addition of an aqueous solution of a volatile acid wherein the solvent has higher volatility than the acid. The solvent is then distilled off so as to leave a solution in water of the salt form of the polymer. A suitable volatile acid is acetic acid, in which event a suitable solvent is n-butyl acetate. The active ingredients particularly include enzymes which can be released by dilution of the medium in which they are contained.

All of the aforementioned references are concerned with entrapment or encapsulation of active ingredients, which are to be released at a later stage and thus do not give any indication of how to achieve permanent entrapment of materials, particularly relatively small sized species A variety of techniques are known for providing encapsulated or entrapped colourants.

WO 91/06277 describes cosmetic formulations which have activatable dormant pigments dispersed in an anhydrous base or vehicle. Ground pigment or liquid carrier dispersion is microencapsulated to form stable, dry, free flowing powder of micro-sized particles. The preferred process of encapsulation is by coacervation e.g. by emulsifying a liquid dispersion in a continuous, external aqueous phase to form micro-sized droplets and a complex of colloidal material is added to the external phase in such a way to form a deposit on or around each droplet thereby forming an outer wall or shell. The microcapsules are intended to rupture and release the dormant pigment when subjected to physical forces.

U.S. Pat. No. 5,234,711 concerns methods of encapsulating pigment particles useful in manufacturing of cosmetic products. It is an objective of this disclosure to employ a vinyl-polymeric encapsulation process for increasing the wettability, dispersibility and heat resistance of the pigment particles. The method encapsulation involves redox or free radical vinyl polymerisation in an aqueous medium.

EP 225799 describes microencapsulated solid non-magnetic colourant material in a liquid, gel, waxy or low temperature melting solid carrier phase that is encapsulated within a polymeric shell. Absorbed onto the shell is a silane or titanate coupling agent which increases the oleophilicity of the surface of the solid colourant material.

U.S. Pat. No. 3,876,603 concerns a method of encapsulating pigments comprising by polymerizing at least one ethylenically unsaturated monomer in a dispersing liquid of aliphatic hydrocarbon solvent. This is carried out in the presence of an active solvent for the polymerized monomer. The method employs from about 0.2 to about 6% by weight of a polymerizable ethylenically unsaturated acid, from about 0.2 to about 6% by weight of an imine, and from about 1 to about 40% by of a dispersion stabilizer comprising a branched copolymer that contains two polymeric segments. One segment is solvated by the dispersing liquid and the second segment is an anchor polymer of different polarity to the first segment and is relatively non-solvated by the dispersing liquid and is capable of anchoring with the polymerized particles of the ethylenically unsaturated monomer. This anchor polymer contains pendant groups which are copolymerizable with ethylenically unsaturated monomers so as to form a pseudo-dispersion.

EP 445342 relates to a cosmetic composition comprising a pigment that has been formed by incorporating a solvated dye into a resin and admixing with a cosmetic carrier. The amount of pigment present is sufficient to provide attractive amount of pigment present sufficient to provide an attractive cosmetic effect when applied to skin, nails or hair. Any cosmetically acceptable soluble dye can be used. Any resin may be used provided it can be pulverised to a fine powder. The solvated dye may be incorporated into the resin by adding to the plasticised or molten resin; or by dissolving the dye in a solution of unpolymerised resin and mutual solvent for the dye and the resin, then polymerising the resin, or by contacting the dye with the resin. The dye inpregnated resin powders are said to be used in a variety of cosmetic compositions.

One of objective of the present invention is to provide polymeric particles containing an entrapped active ingredient which can be retained over a long period of time under a variety of conditions. It is a particular interest to provide products containing entrapped or encapsulated colourants, which products retain the colourant over longer periods and also when subjected to different environments. This is the case for pigments, oil soluble and water soluble dyes, where it is generally difficult to permanently retain them. In a cosmetic composition if the dye or pigment is not permanently retained, this can impair the long term visual effect of the cosmetic.

WO 02/090445 addresses this problem and provides polymeric particles comprising a polymeric matrix and colourant distributed throughout it. The polymeric matrix is formed from a blend of monomers comprising a first monomer which is an ethylenically unsaturated ionic monomer which is a salt of a volatile counterion and a second monomer which is an ethylenically unsaturated hydrophobic monomer which is capable of forming a homopolymer of glass transition temperature in excess of 50° C. Typical matrix polymers include copolymers that have been formed from styrene with ammonium acrylate. The polymeric particles exhibit very good retention properties and are able to retain the colourant under an in a variety of in conditions. However, these particles tend to suffer the drawback that they can fracture and even shatter under certain conditions when handled harshly, and this can lead to loss of the colourant.

A further objective of the present invention is to provide particles that are shatter resistant and can withstand harsh handling. One particular aspect relates to providing shatter resistant particles that contain an active ingredient, especially a colourant.

U.S. Pat. No. 4,056,653 describes spherical shape particles having an average particle diameter of 10 to 100 micron in which the surface is covered with hemispherical shaped bumps of about 0.1 microns in diameter. The particles are formed from a copolymer of alpha olefins and alpha beta ethylenically unsaturated carboxylic acid having 3 to 8 carbon atoms, in which the copolymer has up to 90 percent of carboxylic acid groups ionised by neutralisation with metal ions. The particles form a free flowing powder useful in preparing clear protective shatter resistant coatings for glass.

An objective of the present invention is to provide polymer entrapped colourants in which the particles do not shatter and also the colourant does not leach out even after prolonged use. In one aspect it would be desirable to provide a process for entrapping solutions of dyes in polymeric particles for incorporation into cosmetic formulations and wherein the dyes remain permanently entrapped and are not released before during or after application.

In addition encapsulation or entrapment of colourants can result in visual impairment of the colourant. This may be as a result of the polymer absorbing light from certain wavelengths or sometimes as a result of the irregular morphology of the polymer particles. This is also true where the particles are not shatter resistant. Fractures in the particles or broken particles will also lead to visual impairment of the colourant.

There is a need to provide particles with improved shatter resistance that can be used for a variety of applications. Specifically there is a need to provide products containing entrapped or encapsulated colourants, which products retain the colourant over longer periods and exhibit improved shatter resistance when subjected to different environments. This is also the case when employing pigments, oil soluble and water soluble dyes.

In addition it is also an objective to provide an alternative method for converting oil soluble or water dyes into a product that can be used as a pigment in a variety of applications.

Thus a further objective of the present is to provide polymer containing entrapped colourants which yield improved visual effects It is also an objective to provide particles that combine the features of retaining the colourant and which are shatter resistant under harsh conditions and also exhibit excellent visual properties.

Thus according to the present invention we provide polymeric particles comprising a polymeric matrix that has been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., wherein secondary particles are distributed throughout the matrix, in which the secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the polymeric matrix.

In a further aspect of the present invention we provide a process of preparing polymeric particles comprising a polymeric matrix and secondary particles distributed throughout the matrix, wherein the polymeric matrix that has been formed from a blend of monomers comprising a first monomer which is an ethylenically unsaturated ionic monomer and a second monomer which is an ethylenically unsaturated hydrophobic monomer which is capable of forming a homopolymer of glass transition temperature in excess of 50° C., in which the secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the polymeric matrix.

which process comprises the steps,
A) providing an aqueous phase of a polymeric salt formed from a monomer blend which comprises the first and second monomers,
B) forming the secondary particles in the aqueous phase or combining the secondary particles with the aqueous phase,
C) forming a dispersion comprising the aqueous phase in a water immiscible liquid phase, which preferably comprises an amphipathic polymeric stabiliser to form an emulsion, and
D) subjecting the dispersion to dehydration wherein water is evaporated from the aqueous particles thereby forming solid particles comprising the secondary particles distributed throughout the matrix polymer.

The particles according to the first aspect of the invention and the products resulting from the process according to the second aspect of the invention have enhanced shatter resistance.

Preferably the first monomer used to form the polymeric matrix is a salt of a volatile counterion component. During the dehydration step (D) the volatile counterion component of the salt is desirably evaporated. By this we mean that at least a part of the counterion component is evaporated. For instance, where the polymeric matrix is the ammonium salt, the volatile component ammonia will be evaporated. Consequently, during the distillation stage the matrix polymer would be converted to its free acid or free base form.

Desirably, the particles of the invention can comprise an active ingredient, for instance UV absorbers, UV reflectors, flame retardants, active dye tracer materials. Preferably the polymeric particles comprise a colourant. The colourant may be selected from pigments, dyes or lakes. In the process of preparing the particles it is particularly desirable for the active ingredient, for instance colourant, to be dissolved or dispersed in the aqueous phase so that the active ingredient (e.g. colourant) can become distributed throughout the matrix polymer. We have found that the polymeric particles of the invention exhibit improved shatter resistance in combination with improved visual performance and furthermore the polymer matrix does not allow any of the entrapped active ingredient such as colourant to be released even under prolonged use. It is particularly desirable to provide particles in which the active ingredient, especially colourant, is distributed throughout the polymeric matrix and furthermore the polymeric matrix should be impermeable to the active ingredient (such as colourant).

The polymeric products can be further enhanced if the polymeric matrix is cross-linked. This cross-linking can be as a result of including a cross-linking step in the process. This can be achieved by including self cross-linking groups in the polymer, for instance monomer repeating units carrying a methylol functionality. Preferably though the cross-linking is achieved by including a cross-linking agent with the aqueous phase polymer. The cross-linking agent are generally compounds which react with functional groups on the polymer chain. For instance when the polymer chain contains anionic groups a suitable cross-linking agent may be aziridine, diepoxides, carbodiamides, silanes or a multivalent metal, for instance aluminium, zinc or zirconium. One particularly preferred cross-linking agent are either ammonium zirconium carbonate or zinc oxide. Another particularly preferred class of cross-linking agent include compounds which from covalent bonds between polymer chains, for instance silanes or diepoxides.

The cross-linking process desirably occurs during the dehydration step. Thus where a cross-linking agent is included, it will generally remain dormant until the dehydration is started.

We have found that polymers formed from the special combination of hydrophobic monomer that are capable of forming a homopolymer of glass transition temperature in excess of 50° C., preferably greater than 60 or 80° C. exhibit considerably improved performance in regard to the impermeability to the colourant or other active. By hydrophobic monomer we mean that the monomer has a solubility in water of less than 5 g per 100 ml water.

Figure 1:
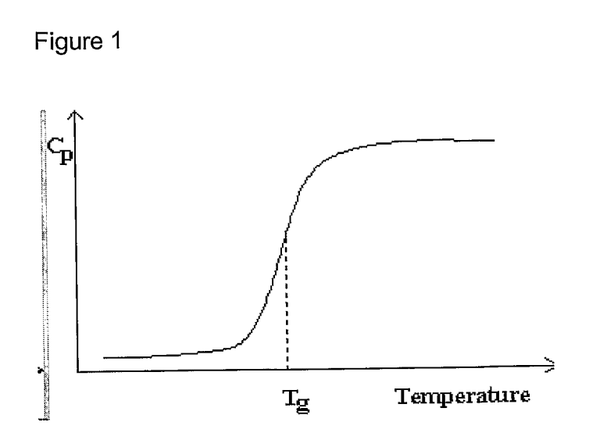

Glass transition temperature (Tg) for a polymer is defined in the Encyclopedia of Chemical Technology, Volume 19, fourth edition, page 891 as the temperature below which (1) the transitional motion of entire molecules and (2) the coiling and uncoiling of 40 to 50 carbon atom segments of chains are both frozen. Thus below its Tg a polymer would not to exhibit flow or rubber elasticity. The Tg of a polymer may be determined using Differential Scanning Calorimetry (DSC). Thus a reference sample with known Tg and the experimental sample are heated separately but in parallel according to a linear temperature programme. The two heaters maintain the two samples at identical temperatures. The power supplied to the two heaters to achieve this is monitored and the difference between them plotted as a function of reference temperature which translates as a recording of the specific heat as a function of temperature. As the reference temperature is increased or decreased and the experimental sample approaches a transition the amount of heat required to maintain the temperature will be greater or lesser depending on whether the transition is endothermic or exothermic. A typical plot indicating the glass transition temperature is shown in FIG. 1.

Generally the average particle size diameter of the particles is less than about 100 microns. Usually the average particle size diameter tends to be smaller, for instance less than 70 or 80 microns, often less than 40 or 50 microns and typically the average particle diameter will be between 750 nanometers and 40 microns. Preferably the average particle size diameter is in the range 10 to 40 microns usually between 10 and 30 microns. Average particle size is determined by a Coulter particle size analyser according to standard procedures well documented in the literature.

Without being limited to theory it is believed that the particular combination of ionic monomer and said hydrophobic monomer provides polymers with the right degree of hydrophilicity and hardness that seems to be responsible for the improvements in impermeability to the colourant or other active. The presence of the secondary particles comprising hydrophobic polymer appear to be responsible for providing the particles of the invention with improved shatter resistance.

Typically the monomer blend in for making the matrix polymer may contain at least 50% by weight hydrophobic monomer, the remainder being made up of ionic monomer or potentially ionic polymer. One or more anionic monomers or one or more cationic monomers may be used as the ionic monomer. It may also be possible to use a blend of cationic and anionic monomers. Generally, the hydrophobic monomer will be present in amounts of at least 60% by weight. Preferred compositions contain between 65 and 90% by weight hydrophobic polymer, for instance around 70 or 75%.

Specific examples of said hydrophobic monomers include styrene, methyl methacrylate, tertiary butyl methacrylate, phenyl methacrylate, cyclohexyl methacrylate and isobornyl methacrylate.

It has been found that it is not possible to replace the hydrophobic monomers with ethylenically unsaturated carboxylic acid esters that are not capable of forming a homopolymer that has a glass transition temperature of at least 50° C. without adversely increasing the permeability of the polymer. Preferably still the Tg should be at least 60° C. or even at least 80° C. For instance substituting the hydrophobic monomer of the present invention by other (meth)acrylic esters, for instance 2-ethyl hexyl acrylate would be unsuitable. Best results are generally obtained by use of monomers which are capable of forming polymers of very high Tg. Therefore less preferred products would be produced using ethyl acrylate or propyl acrylate as the hydrophobic monomer.

The ionic monomer may contain either anionic or cationic groups or alternatively may be potentially ionic, for instance in the form of an acid anhydride. Preferably the ionic monomer is an ethylenically unsaturated anionic or potentially anionic monomer. Suitable anionic or potentially anionic monomers include acrylic acid, methacrylic acid, ethacrylic acid, fumaric acid, maleic acid, maleic anhydride, itaconic acid, itaconic acid anhydride, crotonic acid, vinyl acetic acid, (meth) allyl sulphonic acid, vinyl sulphonic acid and 2-acrylamido-2-methyl propane sulphonic acid. Preferred anionic monomers are carboxylic acids or acid anhydrides.

When the ionic monomer is anionic, for instance a carboxylic acid or anhydride the volatile counterion may be ammonia or a volatile amine component. Generally the volatile amine component will be a liquid that can be evaporated at low to moderate temperatures, for instance by temperatures up to 200° C. Preferably, it will be possible to evaporate the volatile amine under reduced pressure at temperatures below 100° C. Thus the polymer may be produced in free acid form and then neutralised with an aqueous solution of ammonium hydroxide or a volatile amine, for instance ethanolamine, methanolamine, 1-propanolamine, 2-propanolamine, dimethanolamine and diethanolamine. Alternatively the polymer may be prepared by copolymerising the ammonium or volatile amine salt of an anionic monomer with the hydrophobic monomer.

Generally, the matrix polymer may be prepared by any suitable polymerisation process. For instance the polymer can be conveniently prepared by aqueous emulsion polymerisation for instance as described in EP-A-697423 or U.S. Pat. No. 5,070,136. The polymer can then be neutralised by the addition of an aqueous solution of ammonium hydroxide or a volatile amine.

In a typical polymerisation process, the blend of hydrophobic monomer and anionic monomer is emulsified into an aqueous phase which contains a suitable amount of emulsifying agent. Typically, the emulsifying agent may be any commercially available emulsifying agent suitable for forming aqueous emulsion. Desirably these emulsifying agents will tend to be more soluble in the aqueous phase than in the monomer water immiscible phase and thus will tend to exhibit a high hydrophilic lipophilic balance (HLB). Emulsification of the monomer may be effected by known emulsification techniques, including subjecting the monomer/aqueous phase to vigorous stirring or shearing or alternatively passing the monomer/aqueous phase through a screen or mesh. Polymerisation may then be effected by use if suitable initiator systems, for instance UV initiator or thermal initiator. A suitable techniques of initiating the polymerisation would be to elevate the temperature of the aqueous emulsion of monomer to above 70 or 80° C. and then add between 50 and 1000 ppm ammonium persulphate by weight of monomer.

Generally the matrix polymer has a molecular weight of up to 200,000 (Determined by GPC using the industry standard parameters). Preferably the polymer has a molecular weight of below 50,000, for instance 2,000 to 20,000. Usually the optimum molecular weight for the matrix polymer is around 6,000 to 12,000.

A particularly preferred matrix polymer is a copolymer of styrene with ammonium acrylate. More preferably this polymer is used when the process employs a cross-linking agent, which is especially ammonium zirconium carbonate or zinc oxide.

In an alternative version of the process of the present invention the ionic monomer may be cationic or potentially cationic, for instance an ethylenically unsaturated amine. In this form of the invention the volatile counterionic component is a volatile acid component. Thus in this form of the invention the matrix polymer can be formed in an analogous way to the aforementioned anionic matrix polymer, except that the anionic monomer is replaced by a cationic or potentially cationic monomer. Generally where the polymer is prepared in the form of a copolymer of a free amine and hydrophobic monomer, it is neutralised by including a suitable volatile acid, for instance acetic acid, formic acid, propanoic acid, butanoic acid or even carbonic acid. Preferably the polymer is neutralised by a volatile carboxylic acid.

Suitable cationic or potentially cationic monomers include di alkyl amino alkyl (meth) acrylates, di alkyl amino alkyl (meth) acrylamides or allyl amines and other ethylenically unsaturated amines and their acid addition salts. Typically the di alkyl amino alkyl (meth) acrylates include di methyl amino methyl acrylate, di methyl amino methyl methacrylate, di methyl amino ethyl acrylate, di methyl amino ethyl methacrylate, di ethyl amino ethyl acrylate, di ethyl amino ethyl methacrylate, di methyl amino propyl acrylate, di methyl amino propyl methacrylate, di ethyl amino propyl acrylate, di ethyl amino propyl methacrylate di methyl amino butyl acrylate, di methyl amino butyl methacrylate, di ethyl amino butyl acrylate and di ethyl amino butyl methacrylate. Typically the di alkyl amino alkyl (meth) acrylamides include di methyl amino methyl acrylamide, di methyl amino methyl methacrylamide, di methyl amino ethyl acrylamide, di methyl amino ethyl methacrylamide, di ethyl amino ethyl acrylamide, di ethyl amino ethyl methacrylamide, di methyl amino propyl acrylamide, di methyl amino propyl methacrylamide, di ethyl amino propyl acrylamide, di ethyl amino propyl methacrylamide di methyl amino butyl acrylamide, di methyl amino butyl methacrylate, di ethyl amino butyl acrylate and di ethyl amino butyl methacrylamide. Typically the allyl amines include di allyl amine and tri allyl amine.

The secondary particles comprise a hydrophobic polymer that has been formed from an ethylenically unsaturated hydrophobic monomer which is capable of forming a homopolymer of glass transition temperature in excess of 50° C. and optionally other monomers, which hydrophobic polymer is different from the polymeric matrix. The ethylenically unsaturated hydrophobic monomer may be any of the monomers defined above in respect of the second monomer used to form the matrix polymer. Preferably, the hydrophobic monomer is the same as the second monomer used to form the polymeric matrix. Specific examples of said hydrophobic monomers include styrene, methyl methacrylate, tertiary butyl methacrylate, phenyl methacrylate, cyclohexyl methacrylate and isobornyl methacrylate. Preferably the hydrophobic monomer is styrene.

The hydrophobic monomer may be polymerised alone or alternatively may be polymerised with one or more other hydrophobic monomers defined above. It may be possible to include other monomers that are not hydrophobic monomers capable of forming a homopolymer of glass transition temperature in excess of 50° C., provided that such monomers do not bring about any deleterious effects. The other monomer may be in a hydrophobic monomer, for instance longer chain alkyl and esters of acrylic or methacrylic acid, such as 2-ethyl hexyl acrylate or stearyl acrylate. Typically, where such monomers are included, they should be present in an amount of no more than 20% by weight based on to weight of monomers used for the secondary particles. Preferably, these monomers will be present in amount less than 10% by weight and more preferably less than 5% by weight.

Alternatively the other monomer may be a hydrophilic monomer. The hydrophilic monomer may be non-ionic, for instance acrylamide or it could be ionic, for instance as defined in respect of the first monomer used to form the matrix polymer. Generally, such monomers tend to be used in smaller proportions so that the polymer is hydrophobic. Where such monomers are included, they should be present in an amount of no more than 20% by weight based on to weight of monomers used for the secondary particles. Preferably, these monomers will be present in amount less than 10% by weight and more preferably less than 5% by weight.

It is particularly preferred that the secondary particles comprise a hydrophobic polymer that has been formed entirely from one or more ethylenically unsaturated hydrophobic monomer(s) which is/are capable of forming a homopolymer of glass transition temperature in excess of 50° C. A particularly suitable hydrophobic polymer is a copolymer of styrene and methyl methacrylate and a homopolymer of styrene. The polymer of styrene with methyl methacrylate generally will comprise at least 40% by weight styrene and to 60% by weight methyl methacrylate. Preferably, the copolymer will have a weight ratio of styrene to methyl methacrylate of between 50:50 to 95:5 and more preferably 60:40 to 80:20, particularly preferably 70:30 to 75:25.

Generally, the secondary particles will have an average particle size of below 1 micron, and usually below 750 nm. Preferably, the secondary particles will have an average particles size in the range between 50 and 500 nm. The secondary particles may be prepared by any conventional means. Typically, the particles may be prepared by aqueous emulsion polymerisation. Preferably, the particles are prepared by aqueous microemulsion polymerisation according to any typical microemulsion polymerisation process documented in the prior art, for instance as described in EP-A-531005 or EP-A-449450.

Typically, the secondary particles may be prepared by forming a microemulsion comprising a continuous aqueous phase (between 20 and 80% by weight), a dispersed oil phase comprising the monomer (between 10 and 30% by weight), and surfactant and/or stabiliser (between 10 and 70% by weight). Generally the surfactant and/or stabiliser will exist predominantly in the aqueous phase. A preferred surfactant and/or stabiliser is an aqueous solution of the polymer used to form the polymeric matrix. A particularly preferred surfactant/stabiliser is a copolymer of ammonium acrylate with styrene, as defined above in relation to the matrix polymer.

Polymerisation of the monomer in the microemulsion can be effected by a suitable initiation system, for instance UV initiator or thermal initiator. A suitable technique of initiating the polymerisation is, for instance, to elevate the temperature of the aqueous emulsion of monomer to above 70 or 80° C. and then add between 50 and 1000 ppm ammonium persulphate or an azo compound such as azodiisobutyronitrile by weight of monomer. Alternatively, a suitable peroxide, e.g. a room-temperature curing peroxide, or a photo-initiator may be used. It may be preferred that polymerisation is carried out at about room temperature, e.g. with a photo-initiator.

Generally the secondary particles comprise a polymer that has a molecular weight of up to 2,000,000 (Determined by GPC using the industry standard parameters). Preferably the polymer has a molecular weight of below 500,000, for instance 5,000 to 300,000. Usually the optimum molecular weight for the polymeric secondary particles is between 100,000 and 200,000.

It is preferred that the secondary particles have a core shell configuration in which the core comprises the hydrophobic polymer surrounded by a polymeric shell. More preferably the secondary particles comprise a core comprising the hydrophobic polymer and a shell comprising the matrix polymer. It is particularly preferable that the shell of matrix polymer is formed around the core of hydrophobic polymer and during polymerisation.

As indicated previously the particles of the invention can comprise an active ingredient, for instance UV absorbers, UV reflectors, flame retardants, active dye tracer materials or preferably a colourant.

The particles may contain one or more colourants and the colourant may be any colourant, for instance a dye, pigment or lake. Typically suitable colourants include any organic or inorganic pigment or colourant approved for use in cosmetics by CTFA and the FDA such as lakes, iron oxides, titanium dioxide, iron sulphides or other conventional pigments used in cosmetic formulations. Examples of the pigment include an inorganic pigment such as carbon black, D&C Red 7, calcium lake, D&C Red 30, talc Lake, D&C Red 6, barium lake, Russet iron oxide, yellow iron oxide, brown iron oxide, talc, kaolin, mica, mica titanium, red iron oxide, magnesium silicate and titanium oxide; and organic pigment such as Red No 202, Red No 204, Red No 205, Red No 206, Red No 219, Red No 228, Red No 404, Yellow No 205, Yellow No 401, Orange No 401 and Blue No 404. Examples of oil soluble dyes include Red No 505, Red No 501, Red No 225, Yellow No 404, Yellow No 405, Yellow No 204, Orange No 403, Blue No 403, Green No 202 and Purple No 201. Examples of vat dyes are Red No 226, Blue No 204 and Blue No 201. Examples of lake dye include various acid dyes which are laked with aluminium, calcium or barium. Conventional dyes may also be used and may be either oil or water soluble. Suitable dyes for the present invention include FD & C Blue No 11, FD & C Blue No 12, FD&C Green No 13, FD & C Red No 13, FD & C Red No 140, FD&C Yellow No. 15, FD&C Yellow No. 16, D&C Blue No. 14, D&C Blue No. 19, D&C Green No. 15, D&C Green No. 16, D&C Green No. 18, D&C Orange No. 14, D&C Orange No. 15, D&C Orange No. 110, D&C Orange No. 111, D&C Orange No. 117, FD&C Red No. 14, D&C Red No. 16, D&C Red No. 17, D&C Red No. 18, D&C Red No. 19, D&C Red No. 117, D&C Red No. 119, D&C Red No. 121, D&C Red No. 122, D&C Red No. 127, D&C Red No. 128, D&C Red No. 130, D&C Red No. 131, D&C Red No. 134, D&C Red No. 139, FD&C Red No. 140, D&C Violet No. 12, D&C Yellow No. 17, Ext. D&C Yellow No. 17, D&C Yellow No. 18, D&C Yellow No. 111, D&C Brown No. 11, Ext. D&C Violet No. 12, D&C Blue No. 16 and D&C Yellow No. 110. Such dyes are well known, commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc. These publications are incorporated herein by reference.

The colourant can be a substance which is a dormant colourant, for instance a colour former which exhibits a colour on exposure to a suitable trigger mechanism, for instance heat or irradiation. Suitably such entrapped colour formers can be coated onto or incorporated into a suitable substrate and then treated to exhibit the colour. The advantage of providing colour formers as polymeric particles is that they can be more easily be processed and incorporated into the substrate in a desired way. The colour former can still be activated even though it is entrapped within the polymer particle.

The process of the present invention involves dispersing the aqueous solution of matrix polymer containing secondary particles into a water immiscible liquid.

The secondary particles may be comprised within the aqueous solution of the matrix polymer as a result of polymerising the monomers used to form the secondary particles as an aqueous emulsion or aqueous microemulsion polymerisation in the presence of an aqueous solution of the matrix polymer, for instance as described previously. Alternatively, the secondary particles may be separately prepared and then dispersed within the aqueous solution of matrix polymer to form a dispersion. The dispersion can then be subjected to dehydration in order to remove water from the aqueous matrix polymer solution, resulting in the formation of the particles of the invention.

Particles of the present invention that comprise an active ingredient (e.g. a colourant), can be prepared by dispersing the active ingredient in the aqueous solution of matrix polymer. Thus the dispersion would comprise an active ingredient (e.g. colourant) and secondary particles distributed throughout the solution of matrix polymer.

Typically the water immiscible liquid is an organic liquid or blend of organic liquids. The preferred organic liquid is a mixture of a non-volatile paraffin oil and a volatile paraffin oil. The two oils may be used in equal proportions by weight, but generally it is often preferred to use the non-volatile oil in excess, for instance greater than 50 to 75 parts by weight of the non-volatile oil to 25 to less than 50 parts by weight of the volatile oil.

In the process of obtaining the particles according to the invention it is desirable to the present invention to include a polymeric amphipathic stabiliser in the water immiscible liquid. The amphipathic stabiliser may be any suitable commercially available amphipathic stabiliser, for instance HYPERMER® (available from ICI). Suitable stabilisers also include the stabilisers described in WO-A-97/24179. Although it is possible to include other stabilising materials in addition to the amphipathic stabiliser, such as surfactants, it is generally preferred that the sole stabilising material is the amphipathic stabiliser.

In the process of the present invention the dehydration step can be achieved by any convenient means. Desirably, dehydration can be effected by subjecting the dispersion in oil to vacuum distillation. Generally this will require elevated temperatures, for instance temperatures of 30° C. or higher. Although it may be possible to use much higher temperatures e.g. 80 to 90° C. it is generally preferred to use temperatures of below 60 or 70° C.

Instead of vacuum distillation it may be desirable to effect dehydration by spray drying. Suitably this can be achieved by the spray drying process described in WO-A-97/34945.

The dehydration step removes water from the aqueous solution of matrix polymer and also the volatile counterion component, resulting in a dry polymer matrix which is insoluble an non-swellable in water, containing therein the secondary particles and optionally active ingredient (e.g. a colourant) which are distributed throughout the polymeric matrix.

The particles of the invention can be used in a variety of industrial applications, for instance in the manufacture of inks, paper and personal care, such as cosmetic compositions and other personal care formulations.

The following examples are an illustration of the invention.

EXAMPLE 1

Shatter resistant yellow coloured micro-beads comprising 60% by weight pigments and 40% by weight crosslinked matrix polymer are prepared as follows:—

An aqueous phase is prepared by diluting 488 g of 46% polymer microemulsion containing 32% by weight of a styrene-methyl methacrylate copolymer (70/30 weight % monomer ratio, molecular weight 200,000) microemulsion stabilised with a 14 weight % styrene-acrylic acid copolymer (65/35 weight % monomers ratio, molecular weight 6000) with 790 g of water and then milling 313 g of Yellow #10 Al lake powder (ex-Kingfisher) and 56 g titanium dioxide under a high speed mixer. To the resulting aqueous pigment dispersion is added 19 g of 50% aqueous solution of ammonium zirconium carbonate.

Separately, an oil phase is prepared by diluting 76 g of 20% amphipathic stabiliser (90 weight % stearyl methacrylate 10 weight % methacrylic acid copolymer, molecular weight 40,000) with 1800 g of Isopar G solvent (available from Exxon Mobil). The above aqueous phase is added to this oil phase under a high shear homogeniser to form a water-in-oil emulsion having a mean aqueous droplet particle diameter of 20 microns. The formed emulsion is transferred to a 1-liter reactor set-up for vacuum distillation. The emulsion is warmed to 60° C. and then subjected to vacuum distillation to remove water/Isopar G solvent mixture. Vacuum distillation is continued to 100° C. until no further water is collected in the distillate. Next, the reactor contents are held for further 1 hour to complete the crosslinking reaction between the zirconium crosslinker and the carboxylated supported resin.

After this heat treatment step, the reactor contents are cooled to 25° C. and the coloured micro-beads formed are isolated by filtration and oven drying at 90° C.

The final product is free flowing yellow micro-beads having a mean particle size diameter of 20 microns.

EXAMPLE 2

A red coloured micro-beads was prepared in the same manner as described in Example 1 except 313 g of Red #7 Ca lake powder (ex-Kingfisher) was used instead of the Yellow #10 Al lake powder.

EXAMPLE 3

A blue coloured micro-beads was prepared in the same manner as described in Example 1 except 313 g of Blue #1 Al lake powder (ex-Kingfisher) was used instead of the Yellow #10 Al lake powder.

EXAMPLE 4

This example illustrates the shatter resistance of the coloured microbeads obtained by this invention. 30 grams of yellow micro-beads of Example 1 were added to 270 g of Isopropyl myristate. The resulting micro-bead slurry warmed to 75° C. and then homogenized for 30 minutes at 6,000 rpm with a high shear mixer. After, this treatment the mixture was cooled to room temperature and the micro-beads examined under a light microscope. FIG. 2 shows the coloured particles made according to this invention.

EXAMPLE 5

An aqueous phase is prepared by diluting 200 g of a 46% polymer micro emulsion (a styrene-methyl methacrylate copolymer micro emulsion stabilised with a styrene-acrylic acid copolymer) with 100 g of water. Into this 31 g of Blue #1 Al lake powder (ex Kingfisher) is dispersed under a high shear mixer. To the resultant dispersion a slurry, comprising 20 g of Zinc Oxide Hydrate in 80 g water, is added.

Separately, an oil phase is prepared by dilution 44 g of a 20% amphipathic stabiliser (comprised of a stearyl methacrylate (90 wt %)—Methacrylic acid copolymer (10 wt %)) with 600 g of Isopar G (ex Exxon Mobil).

The aqueous phase is dispersed into the oil phase with the aid of a high shear homogeniser to form a water-in-oil emulsion with a mean particle diameter of 20 microns. This emulsion is transferred into a set of apparatus equipped for distillation. The emulsion is warmed to 50° C. and subjected to vacuum distillation and heating (maximum temperature 100° C.) until no more water is collected in the distillate. After this, the reactor contents are held at about 100° C. for a further hour to complete the crosslinking reaction. Once this is complete, the reaction mass is cooled to 25° C. and filtered to recover the coloured beads. Finally the beads are oven dried at 90° C. to yield a free flowing blue powder with a mean particle diameter of 20 microns.

The invention claimed is:

1. Polymeric particles comprising a polymeric matrix, an active ingredient and secondary particles, which active ingredient and secondary particles are distributed throughout the matrix, which matrix polymer is a copolymer consisting of (meth)acrylic acid or salt units thereof and styrene units, wherein
    the secondary particles consist of a hydrophobic polymer consisting of methyl methacrylate units and 70 wt. % styrene units and,
    the secondary particles have a core shell configuration in which the core comprises the hydrophobic polymer and the shell comprises the matrix polymer, and the polymeric matrix is crosslinked.

2. Polymeric particles according to claim 1, in which the (meth)acrylic acid or salt thereof is a salt of a volatile counterion component.

3. Polymeric particles according to claim 2 in which the (meth)acrylic acid or salt thereof is an acid salt of a volatile counterion component, wherein the volatile counterion component is ammonia or a volatile amine.

4. Polymeric particles according to claim 2 in which the (meth)acrylic acid or salt thereof is an amine salt of a volatile counterion component, wherein the volatile counterion component is a volatile carboxylic acid.

5. Polymeric particles according to claim 1, which comprise an active ingredient selected from the group consisting of UV absorbers, UV reflectors, flame retardants and active dye tracer materials.

6. Polymeric particles according to claim 1, in which the (meth)acrylic acid or salt thereof is a free acid.

7. Polymeric particles according to claim 1 in which the polymeric particles have an average particle size of below 100 microns.

8. Polymeric particles according to claim 1 in which the (meth)acrylic acid or salt thereof is a salt of ammonium acrylate, and ammonium zirconium carbonate or zinc oxide is used as a cross-linking agent.

9. Polymeric particles according to claim 1 in which the secondary particles have an average particle size of below 750 nm.

10. Polymeric particles according to claim 9 in which the secondary particles have an average particle size in the range between 50 and 500 nm.

11. Polymeric particles according to claim 1 in which the matrix polymer is impermeable to the active ingredient.

12. A process of preparing polymeric particles comprising a polymeric matrix, an active ingredient and secondary particles which active ingredient and secondary particles are distributed throughout the matrix,
    wherein the polymeric matrix is a copolymer consisting of (meth)acrylic acid or salt units thereof and styrene units,
    in which the secondary particles consist of a hydrophobic polymer consisting of methyl methacrylate units and 70 wt. % styrene units, which process comprises the steps,
        A) providing an aqueous phase of a polymeric salt formed from a copolymer consisting of (meth)acrylic acid or salt units thereof and styrene units and the active ingredient,
        B) forming the secondary particles in the aqueous phase or combining the secondary particles with the aqueous phase,
        C) forming a dispersion consisting essentially of the aqueous phase in a water immiscible liquid phase which comprises an amphipathic polymeric stabiliser to form an emulsion, and
        D) subjecting the dispersion to dehydration wherein water is evaporated from the aqueous particles thereby forming solid particles comprising the secondary particles distributed throughout the matrix polymer,
    wherein the secondary particles have a core shell configuration in which the core comprises the hydrophobic polymer and the shell comprises the matrix polymer and the polymeric matrix is crosslinked.

13. A process according to claim 12, in which the (meth) acrylic acid or salt thereof is a salt of a volatile counterion component.

14. A process according to claim 13 in which the (meth) acrylic acid or salt thereof is a salt of a volatile counterion component, wherein the volatile counterion component is ammonia or a volatile amine.

15. A process according to claim 12, in which the particles comprise an active ingredient selected from colourant.

16. A process according to claim 15 in which the colourant is a dye, pigment or lake.

17. A process according to claim 12, in which the (meth) acrylic acid or salt thereof is a free acid.

18. A process according to claim 12, in which a cross-linking agent is included in the aqueous phase and the matrix polymer becomes cross-linked during the dehydration step.

19. A process according to claim 18 in which the matrix polymer is impermeable to the active ingredient.

20. A process according to claim 18 in which the dehydration step involves vacuum distillation.

21. A process according to claim 12 in which the polymeric particles have an average particle size of below 100 microns.

22. A process according to claim 12 in which the polymeric matrix is a copolymer consisting of monomer units of styrene and ammonium acrylate, and ammonium zirconium carbonate or zinc oxide is used as a cross-linking agent.

23. A process according to claim 12 in which the secondary particles have an average particle size of below 750 nm.

24. A process according to claim 23 in which the secondary particles have an average particle size in the range between 50 and 500 nm.

25. A process according to claim 12 in which particles are formed as a micro emulsion within the aqueous phase by microemulsion polymerisation.

26. A process according to claim 12 in which the dehydration step involves spray drying.

* * * * *